(12) United States Patent
Bai et al.

(10) Patent No.: US 8,241,635 B2
(45) Date of Patent: Aug. 14, 2012

(54) SILVER IONIZED PLANT EXTRACTION LIQUID AND USE THEREOF

(75) Inventors: Dong-gyu Bai, Gwangju (KR); Jeong-ho Lee, Jangheung-gun (KR); Kyu-jeong Cho, Gwangju (KR); Sun-mi Huh, Gwangju (KR); Sang-hwa Park, Gwangju (KR)

(73) Assignees: Damyangkun, Jeollanam-do (KR); Dong-gyu Bai, Gwangju (KR)

( * ) Notice: Subject to any disclaimer, the term of this patent is extended or adjusted under 35 U.S.C. 154(b) by 73 days.

(21) Appl. No.: 12/762,286

(22) Filed: Apr. 16, 2010

(65) Prior Publication Data

US 2010/0196414 A1 Aug. 5, 2010

Related U.S. Application Data

(62) Division of application No. 11/816,278, filed as application No. PCT/KR2006/000456 on Feb. 8, 2006, now abandoned.

(30) Foreign Application Priority Data

Feb. 14, 2005 (KR) .................. 10-2005-0011888

(51) Int. Cl.
*A61K 36/22* (2006.01)
*A61K 36/00* (2006.01)
*A61K 36/15* (2006.01)
*A61K 36/02* (2006.01)
*A61K 36/13* (2006.01)
*A61K 36/20* (2006.01)

(52) U.S. Cl. .................. 424/195.17; 424/725; 424/770; 424/771

(58) Field of Classification Search .................. None
See application file for complete search history.

(56) References Cited

FOREIGN PATENT DOCUMENTS

| CN | 1537630 A | | 10/2004 |
|----|-----------|---|---------|
| JP | 2003-113010 A | | 4/2003 |
| JP | 2003252787 A | * | 9/2003 |
| JP | 2004-161632 A | | 6/2004 |
| KR | 2000-0012407 | | 3/2000 |
| KR | 2001-0001271 A | | 1/2001 |
| KR | 2003-0015973 A | | 3/2003 |
| KR | 2005-0006698 A | | 1/2005 |

OTHER PUBLICATIONS

Spadaro et al, Antibacterial effects of silver electrodes with weak direct current, Antimicrobial Agents and Chemotherapy, 6 (5): 637-642, 1974.*

WIPO, International Search Report, mailing date Apr. 20, 2006, for corresponding International Application No. PCT/KR2006/000456.

* cited by examiner

*Primary Examiner* — Qiuwen Mi
(74) *Attorney, Agent, or Firm* — Intellectual Property Law Group LLP

(57) ABSTRACT

The present invention relates to silver-ionized plant extraction liquid and the use thereof. Particularly, there are provided herein a silver-ionized liquid extraction liquid prepared by ionizing silver in a plant extraction liquid used as an electrolyte and an antimicrobial composition comprising the same.

2 Claims, 8 Drawing Sheets

SILVER IONIZED PLANT EXTRACTION LIQUID AND USE THEREOF

CROSS-REFERENCE

This is a divisional of U.S. application Ser. No. 11/816,278, filed on Aug. 14, 2007 (now abandoned) which is hereby incorporated herein by reference. application Ser. No. 11/816,278 is a U.S. National Phase application under 35 U.S.C. §371 of International Application no. PCT/KR2006/00456 with an international filing date of Feb. 8, 2006 and claims benefit of Korea Application no. 10-2005-0011888 filed on Feb. 14, 2005.

TECHNICAL FIELD

The present invention discloses a silver-ionized plant extraction liquid and the use thereof. Particularly, there are provided herein a silver-ionized plant extraction liquid prepared by ionizing silver in a plant extraction liquid used as an electrolyte and an antimicrobial composition comprising the same.

RELATED PRIOR ART

Silver is a metal that has been long known to have a wide-ranged antimicrobial activity as mentioned in various old documents. Silver has thus been used in preparing tableware such as a spoon in real life.

The microbial activity of silver actually comes from the silver ion ($Ag^+$), and, for this reason, there have been many attempts to prepare silver-ionized water more easily and efficiently. For example, Korean patent publication Nos. 10-2003-0090466 and 10-2005-0001240, both of which have the title "device for producing silver-ionized water" commonly, disclose the techniques for production of silver-ionized water.

Meanwhile, the plant extraction liquid is also known to generally have an antimicrobial activity in a more or less degree regardless of the kind of the plant and the method of extraction [Hori Y, Sato S, Hatai A. Antibacterial activity of plant extracts from azuki beans (*Vigna angularis*) in vitro. Phytother Res. 2006 Jan. 27; 20(2):162-164; Ravikumar S, Nazar S, Nuralshiefa A, Abideen S. Antibacterial activity of traditional therapeutic coastal medicinal plants against some pathogens. J Environ Biol. 2005 June; 26(2 Suppl):383-6; Bandyopadhyay D, Chatterjee T K, Dasgupta A, Lourduraja J, Dastidar S G. In vitro and in vivo antimicrobial action of tea: the commonest beverage of Asia. Biol Pharm Bull. 2005 November; 28(11):2125-7].

The present inventors ionized silver in a plant extraction liquid used as an electrolyte, considering that both silver and a plant extraction liquid have general antimicrobial activities, as a result, became to recognize that the resultant silver-ionized plant extraction liquid shows a remarkably superior antimicrobial activity. The present invention has been completed in this way.

DISCLOSURE

Technical Problem

Therefore, the present invention aims to provide a silver-ionized plant extraction liquid prepared by ionizing silver in a plant extraction liquid by means of electrolysis.

The present invention also aims to provide an antimicrobial composition comprising the aforementioned silver-ionized plant extraction liquid.

Hereunder are set forth other objects and embodiments of the present invention.

Technical Solution

According to one aspect of the present invention, there is provided a silver-ionized plant extraction liquid. The silver-ionized plant extraction liquid is prepared by ionizing silver in plant extraction liquid used as an electrolyte (a liquid which electricity can pass through in electrolysis) by means of electrolysis.

The present inventors performed numerous experiments where a plant extraction liquid as a electrolyte (it is prepared from a plant such as a bamboo, an oak, a pine, an oriental arbor vitae (*thuja*) and a marine algae) was placed in an electrolytic bath and silver-ionization was induced by applying voltage to two silver electrodes immersed in the plant extraction liquid, and recognized that the resultant substance showed a synergistic increase in an antimicrobial activity as compared to the plant extraction liquid used as an electrolyte or the silver-ionized water, which was prepared by using triple distilled water instead of the plant extraction liquid as an electrolyte, as shown in the Examples and Experimental Examples herein.

Therefore, the silver-ionized plant extraction liquid may be understood as a plant extraction liquid having an antimicrobial activity prepared by ionizing silver in a plant extraction liquid used as an electrolyte by means of electrolysis.

As used herein, the terms of "an antimicrobial activity" and "a microorganism" and the scope of the microorganism are as described below in connection with the following antimicrobial composition according to the present invention.

Meanwhile, the electrolysis may be performed in any way insofar as silver is ionized in a plant extraction liquid used as an electrolyte, because the sliver-ionized plant extraction liquid according to the present invention is prepared by ionizing silver in a plant extraction liquid used as a electrolyte by means of electrolysis by applying voltage to two silver electrodes immersed in the plant extraction liquid.

Therefore, although a cathode from which silver ion is produced should be a conductor comprising silver, an anode does not have to be a conductor comprising silver but have only to be a conductor such as metal or graphite.

Further, the purity of silver in a conductor comprising silver (i.e. the degree of how much a conductor comprises a silver) does not matter because silver may be ionized even in lower purity by applying higher voltage as known in the prior art. Nonetheless, it is preferable that silver of higher purity is used as a cathode in consideration of the higher antimicrobial activity of the resultant sliver-ionized plant extraction liquid.

Furthermore, the time and the voltage in electrolysis do not matter only if they are enough to induce the silver ionization. However, it is preferred to adopt longer time and higher voltage in that the antimicrobial activity of the sliver-ionized plant extraction liquid is increased as the electrolysis time is longer and the voltage is higher as shown in Experimental Examples 1(4) and 2(4) and Tables 5 and 8.

Meanwhile, a plant extraction liquid to be used as an electrolyte herein has only to be of a liquid phase. Thus, the plant extraction liquid may be immediately used if it is originally obtained in a liquid phase. The solid-phased plant extract may be dissolved in an appropriate solvent such as water, distilled water and alcohol that can be used as an electrolyte. It may be preferred that even the liquid-phased plant extraction liquid is diluted in an appropriate solvent to be used as an electrolyte.

Meanwhile, any plant extraction liquid should be understood to be used as an electrolyte in the present invention regardless of the kind of the plant in that all kinds of the plant extraction liquids that the present inventors selected as an electrolyte in the following Experimental Examples showed synergistically increased antimicrobial activities without exception when they were silver-ionized. Therefore, any plant may be used to obtain the plant extraction liquid to be used as an electrolyte in the present invention only if the plant may be categorized as a plant according to the standard of taxonomy.

Taxonomically, a plant refers to a living organism that has a cell wall outside a cell membrane and that is capable of photosynthesis and thus is capable of autotrophy. Examples of the plant includes without limitation algae (e.g. *Cyanophyta, Cryptophyta, Chrysophyta, Bacillariophyta, Phaeophyta, Rholophyta, Chlorophyta, Charophyta*), bryophytes, pteridophytes and spermatophytes (e.g. Angiospermae and Gymnospermae).

Meanwhile, a pine extraction liquid showed no antimicrobial activity against any of the microorganisms that the present inventors randomly selected, however, as shown in Experimental Example 3 and Table 9, the silver-ionized pine extraction liquid exhibited a high antimicrobial activity against all the microorganisms that the present inventors selected. Likewise, an Oriental arbor vitae (or a *thuja*) extraction liquid or a marine algae extraction liquid shows a weak antimicrobial activity against only some of the microorganisms that the present inventors randomly selected. However, as shown in Experimental Examples 4 & 5 and Tables 10 & 11, a silver-ionized pine extraction liquid and a silver-ionized marine algae extraction liquid exhibited a very high antimicrobial activity against all the microorganisms that the present inventors selected.

Therefore, it should be noted that even a plant extraction liquid without any antimicrobial activity may be used as an electrolyte in preparing the silver-ionized plant extraction liquid of the present invention.

It should also be noted that any plant extraction liquid may be used as an electrolyte in preparing the silver-ionized plant extraction liquid of the present invention regardless of the extraction method.

Generally, there are four methods for preparing a plant extraction liquid as follows: (i) to heat the target plant directly or indirectly and obtain resinous plant extraction liquid, (ii) to cut the upper part of the plant and collect running-out plant extraction liquid, (iii) to immerse the plant in appropriate extraction solvent (e.g. methanol, distilled water, ethanol, acetone, ethyl acetate, saturated n-butanol, chloroform, methylene chloride, water or mixture thereof) and obtain extraction liquid, and (iv) to dry and burn the plant and collect and cool the combustion gas.

Typically, the methods (i), (ii) and (iv) are appropriate for plants having a woody part (xylem) while the method (iii) may be used for any kind of plant.

Therefore, it should be noted that the method (iii) may also be used in the present invention although the following Reference Examples adopt only the methods (i), (ii) and (iv). Further, the present inventors also verified a high antimicrobial activity in the case of a plant extraction liquid prepared by extracting sawdust-shaped bamboo with 70% ethanol, dissolving the freeze-dried extraction powders in triple distilled water and ionizing silver using the resultant solution as an electrolyte, although it is not shown in the following Experimental Examples.

Therefore, it should also be noted that any plant extraction liquid may be used in preparing the silver-ionized plant extraction liquid of the present invention regardless of the extraction method.

Although any kind of plant and extraction method may be used in the present invention as mentioned previously, it is preferred to employ the plants used in the following Reference Examples, e.g. a bamboo, an oak, a pine, an oriental arbor vitae (*thuja*) and a marine algae in combination with the aforementioned extraction methods, more preferably the method of (i), (ii) or (iv).

As used herein, the term of 'a marine algae' refers to sea-dwelling algae including brown alga, green alga and red alga, and the terms of 'bamboo', 'oak', 'pine' and '*thuja*' should be understood to include any plant that may be thus categorized according to the standard of taxonomy.

According to another aspect of the present invention, there is provided a process of preparing a silver-ionized plant extraction liquid. This process herein comprises a step of ionizing silver by means of electrolysis in an electrolyte of a plant extraction liquid.

According to still another aspect of the present invention, there is provided a process of increasing an antimicrobial activity of an antimicrobial plant extraction liquid. This process herein comprises a step of ionizing silver in the antimicrobial plant extraction liquid used as an electrolyte by means of electrolysis.

According to a further aspect of the present invention, there is provided a process of introducing an antimicrobial activity into a non-antimicrobial plant extraction liquid. This process herein comprises a step of ionizing silver in the non-antimicrobial plant extraction liquid used as an electrolyte by means of electrolysis.

As used in connection with 'a process of preparing a silver-ionized plant extraction liquid', 'a process of increasing an antimicrobial activity of an antimicrobial plant extraction liquid' and 'a process of introducing an antimicrobial activity into a non-antimicrobial plant extraction liquid', the meanings of the terms of 'silver-ionized plant extraction liquid', 'an antimicrobial activity', 'a microorganism' and 'a plant extraction liquid' along with the range of the microorganism and descriptions on the electrolysis time and voltage and silver purity are the same as set forth herein.

According to a still further aspect of the present invention, there is provided an antimicrobial composition comprising the aforementioned silver-ionized plant extraction liquid as an active ingredient.

As used herein, 'an antimicrobial activity' refers to an activity of inhibiting the growth or proliferation of microorganisms or killing microorganisms.

As used herein, 'a microorganism' includes bacteria, fungi, yeast and algae, against which the silver-ionized plant extraction liquid herein may have an antimicrobial activity.

As verified in the following Experimental Examples, the silver-ionized plant extraction liquid, which is contained in the antimicrobial composition of the present invention as an active ingredient, shows a microbial activity against all the microorganisms that the present inventors selected regardless of the kind of the plant from that the plant extraction is prepared.

Based on the disclosure in following Experimental Examples, one skilled in the art is expected to easily verify and select other microorganisms against which the silver-ionized plant extraction liquid in the antimicrobial composition herein may have an antimicrobial activity using one's ordinary skill.

Therefore, the term of 'an microorganism' herein includes all other microorganisms, against which the silver-ionized plant extraction liquid in the antimicrobial composition herein is expected to have an antimicrobial activity, in addition to the microorganisms as shown in the following Examples against that the silver-ionized plant extraction liquid has an antimicrobial activity.

The term of 'an microorganism' herein includes at least two classes of microorganisms, against which the plant extraction liquid and the silver-ionized water may have antimicrobial activities, respectively. The reason is that it is evident that the silver-ionized plant extraction liquid herein will show an antimicrobial activity against the microorganisms that a silver-ionized solution or a plant extraction liquid has an antimicrobial activity against, in that the silver-ionized plant extraction liquid herein showed synergistic effects against all the microorganisms that a silver-ionized solution or a plant extraction liquid has an antimicrobial activity against as shown in the following Experimental Examples. As used herein, 'silver-ionized solution' includes any solution containing silver ions, prepared by ionizing silver by electrolysis in a solvent used as an electrolyte such as water, distilled water and alcohol.

However, it is preferable that the term of 'an microorganism' herein is understood to mean bacteria, fungi, yeast and algae against that the silver-ionized plant extraction liquid is proved to have antimicrobial activity in the following Experimental Examples, particularly to mean *Escherichia* sp., *Salmonella* sp., *Bacillus* sp., *Staphylococcus* sp., *Vibrio* sp., *Aeromonas* sp., *Chromobacteria* sp., *Streptococcus* sp., *Lactobacillus* sp. among bacteria, *Aspergillus* sp., *Fusarium* sp., *Trichoderma* sp., *Trichophyton* sp., *Microsporum* sp. among fungi and *Candida* sp. among yeast. Most preferably, the term of 'an microorganism' herein means each of the microorganisms against that the silver-ionized plant extraction liquid herein is directly proved to have antimicrobial activity in the following Experimental Examples.

The aforementioned antimicrobial composition herein may be used alone or in combination of other antimicrobial agent for improving or preventing a harmful phenomenon caused by microorganisms directly or indirectly.

As used herein, "a harmful phenomenon" refers to such phenomenon that the improvement or prevention of the phenomenon would be profitable to human. Examples of the phenomenon include without limitation diseases incurred to human, an animal or a plant, food spoilage, water or soil pollution and deterioration of fibers.

As used herein, "a harmful phenomenon caused by microorganisms directly" (hereinafter "the directly caused phenomenon") means a phenomenon that may be improved or prevented by inhibiting the microorganism growth or proliferation or sterilizing the microorganism. Examples of such phenomenon include but are not limited to typhus or food poisoning caused by *Salmonella* [reference 30 below]; phlegmone, lymphatics or otitis media caused by *Staphylococcus* [references 20-25]; anthracnose or anthrax caused by *Bacillus* [references 34-35]; crop epidemic caused by *Fusarium* [references 37-40]; vaginitis caused by *Candida* or *Lactobacillus*; skin external wound related to *Aeromonas* or *Chromobacterium*; tooth decay caused by *Streptococcus*, trichophytia caused by *Trichophyton* or *Microsporum*. The aforementioned phenomenon may be improved or prevented although the antimicrobial composition of the present invention is alone used.

Likewise, the term of "a harmful phenomenon caused by microorganisms indirectly" (hereinafter the "indirectly caused phenomenon") refers to such phenomenon that inhibition of the microorganism growth or proliferation or sterilization of the microorganism is preferred (i.e. further required) to improve or prevent the phenomenon. Examples of the phenomenon include but are not limited to septicemia caused by *vibrio* [references 32-33] and damage in kidney tissue caused by *E. coli* 0157 [references 26-29].

The indirectly caused phenomenon may be more improved or prevented when the antimicrobial composition of the present invention is used in combination with other antimicrobial agents or any other agents for improving or preventing this phenomenon. For example, for improving or preventing septicemia, the antimicrobial composition herein may be used with any medicine that is effective in treatment or prevention in septicemia such as Xigris (Lilly Co.).

Meanwhile, the amount of the silver-ionized plant extraction liquid to be contained in the antimicrobial composition of the present invention may be determined in consideration of the field to be applied, the required degree of antimicrobial activity (the harmful degree of the harmful phenomenon), etc. For sufficient antimicrobial activity, the silver-ionized plant extraction liquid may be used in an amount above 0.1 wt %, preferably above 3 wt % based on the total weight of the composition herein, regardless of the field to be applied and the required degree of antimicrobial activity.

The antimicrobial composition herein may further comprise a dispersing agent, carrier and other antimicrobial agent insofar as the ingredients do not hinder the activity of the composition herein.

Examples of the dispersing agent, which may be contained alone or in composition with other agents in the antimicrobial composition, include without limitation water, alcohol (e.g. methanol, ethanol, ethylene glycol, propylene glycol, diethylene glycol and glycerin), ketone (e.g. acetone, methyl ethyl ketone), ether (e.g. dioxane, tetrahydrofuran, cellosolve, diethylene glycol dimethyl ether), aliphatic hydrocarbon (e.g. hexane, kerosene), aromatic hydrocarbon (e.g. benzene, toluene, xylene, naphthalene, methyl naphthalene), halogenated hydrocarbon (e.g. chloroform, carbon tetrachloride), acid amide (e.g. dimethyl formamide), ester (e.g. methyl acetate, ethyl acetate, butyl acetate, fatty acid glycerin eater), nitrile (e.g. acetonitrile), surfactant (higher alcohol sulfate ester, alkyl sulfonic acid, alkyl aryl sulfonic acid, tertiary ammonium salt, oxyalkyl amine, fatty acid ester, and polyalkylene oxide compound, anhydrous sorbitol compound).

Examples of the carrier include without limitation clay (e.g. kaolin, bentonite, acidic clay), talc (e.g. talc powder, agalmatolite), silica (e.g. diatomite, silica anhydride, mica powder), alumina, sulfur powder, and activated charcoal. These carriers may be also contained alone or in composition with other agents in the antimicrobial composition.

Examples of the antimicrobial agent include without limitation carvacrol, thymol, citral (Korean patent no. 438209), isoeugenol, methyleugenol (Korean patent no. 427584), bamboo extraction liquid (WO 2003/105878), *Ganoderma sinense* extraction liquid (Korean patent no. 445405), isothiazolone compound, and aminocarboxylic acid (WO 2000/13510) and their mixture, and also may be contained alone or in composition with other agents in the antimicrobial composition.

Meanwhile, the antimicrobial composition herein may be prepared in liquid, solid or gaseous formulation, and may be administered orally or parenterally, and preferably locally. Examples of oral formulation include without limitation tablet, pill, powder, liquid and food. Examples of parenteral formulation include without limitation injection, preparation for local administration (e.g. cream, ointment), suppository and spray (particularly, for plant). Especially, the preparation for local administration includes the preparation where the composition herein is immersed in carriers such as natural or synthetic fiber and the preparation where the composition herein is contained in cosmetics or soap.

If the antimicrobial composition may improve or prevent the above-described harmful phenomenon, the antimicrobial composition may be administered/sprayed to animals such a pat, a domestic animal and a bred fish or plants, and may be also contained in foods as a preservative, and may be contained in or coated on fiber products for enhancing their preservation in preparation of the fiber products.

Hereinafter, the pharmaceutical composition as an aspect of the microbial composition is described in detail in that the microbial composition is expected to be mainly used as a pharmaceutical composition.

In the case that the antimicrobial composition is used as a pharmaceutical composition, the pharmaceutical activity may be considered as improvement or prevention of diseases caused by microorganisms against which the silver-ionized plant extraction liquid to be contained as an effective agent in the antimicrobial composition has an antimicrobial activity.

Preferably, the pharmaceutical activity may be understood to be an activity for improvement or prevention of diseases caused by bacteria, fungi, yeast and algae, against that the silver-ionized plant extract liquid is directly proved to have an antimicrobial activity in the following Experimental Examples, more preferably *Escherichia* sp., *Salmonella* sp., *Bacillus* sp., *Staphylococcus* sp., *Vibrio* sp., *Aspergillus* sp., *Fusarium* sp., *Trichoderma* sp., *Candida* sp., *Lactobacillus* sp., *Aeromonas* sp., *Chromobacterium* sp., *Streptococcus* sp., *Trichophyton* sp., *Microsporum* sp.

Specifically, the antimicrobial composition has an activity for improvement or prevention of damage in kidney tissue caused by *E. coli*, especially *E. coli* 0157 [references 26-29], typhus or food poisoning caused by *Salmonella* [reference 30 below], cholera, septicemia or enteritis caused by *Vibrio* [references 31-32], furuncle, phlegmon, lymphangitis, felon, otitis media, pneumonia, food poisoning or septicemia caused by *Staphylococcus* [references 20-25], gonorrhea, tubercle, syphilis, diphtheria, typhoid fever, measles or inflammation in oral or vaginal mucosa (including vaginitis), pruritis in oral or vaginal mucosa, pain in oral or vaginal mucosa caused by *Candida* [references 1-18], septicemia caused by *Aspergillus* [references 36 and 37], and vaginitis caused by *Lactobacillus*, skin external wound related to *Aeromonas* or *Chromobacterium*, tooth decay or paradentitis caused by *Streptococcus*, and trichophytia caused by *Trichophyton* or *Microsporum*.

The aforementioned diseases should be understood to be exemplified because it is obvious that the pharmaceutical composition has a remedial or preventing activity for the diseases caused by the above-mentioned microorganisms in that the silver-ionized plant extraction liquid has an antimicrobial activity against the above-mentioned microorganisms as shown in the following Experimental Examples. Therefore, it should not be understood that the pharmaceutical composition has a remedial or preventing activity only for the above-exemplified diseases.

At least, the pharmaceutical composition should be understood to be effective in prevention or treatment of the diseases that are known to be caused by the aforementioned microorganisms in the below-mentioned references.

Meanwhile, the pharmaceutical composition may further comprise pharmaceutically acceptable carrier such as lactose, dextrose, sucrose, sorbitol, mannitol, starch, acacia rubber, calcium phosphate, alginate, gelatin, calcium silicate, microcrystalline cellulose, poly(vinyl pyrrolidone), cellulose, water, syrup, methylcellulose, methylhydroxybenzoate, propylhydroxybenzoate, talc, magnesium stearate and mineral oil.

The pharmaceutical composition may further comprise a lubricant, a wetting agent, a sweetening agent, flavors, an emulsifying agent, a suspending agent and a stabilizer as additives.

The carrier may be contained in the pharmaceutical composition in an amount of about 0.1-99.9 wt %, preferably about 0.1-97 wt %, and the additives in an amount of about 0.1-20 wt %, relative to the total weight of the composition.

Although the pharmaceutical composition may be administered orally or parenterally, it is preferred to be directly administered to the target region locally.

The pharmaceutical composition may be prepared in unit dosage form or by being injected into multidose container by using pharmaceutically acceptable carriers or fillers according to the conventional method. Representative examples of formulation type include solution, suspension, emulsion, extraction liquid, powder, granule, tablet and ointment.

A daily dose of the pharmaceutical composition herein is 0.001-150 mL/kg weight and administered once or several times a day. However, appropriate dosage level of the pharmaceutical composition herein may be determined by considering various information such as administration type, patient's age, patient's body weight, patient's sex, patient's condition and administration time. Physicians with average skill may easily determine and diagnose dosage level of medicine effective for treating or preventing target disorders or diseases.

Advantageous Effects

The present invention discloses a silver-ionized plant extraction liquid and an antimicrobial use of the silver-ionized plant extraction liquid. The silver-ionized plant extraction liquid herein shows an antimicrobial activity against various microorganisms, and may be used for improving or preventing a disease caused by microorganisms.

Figure 5:
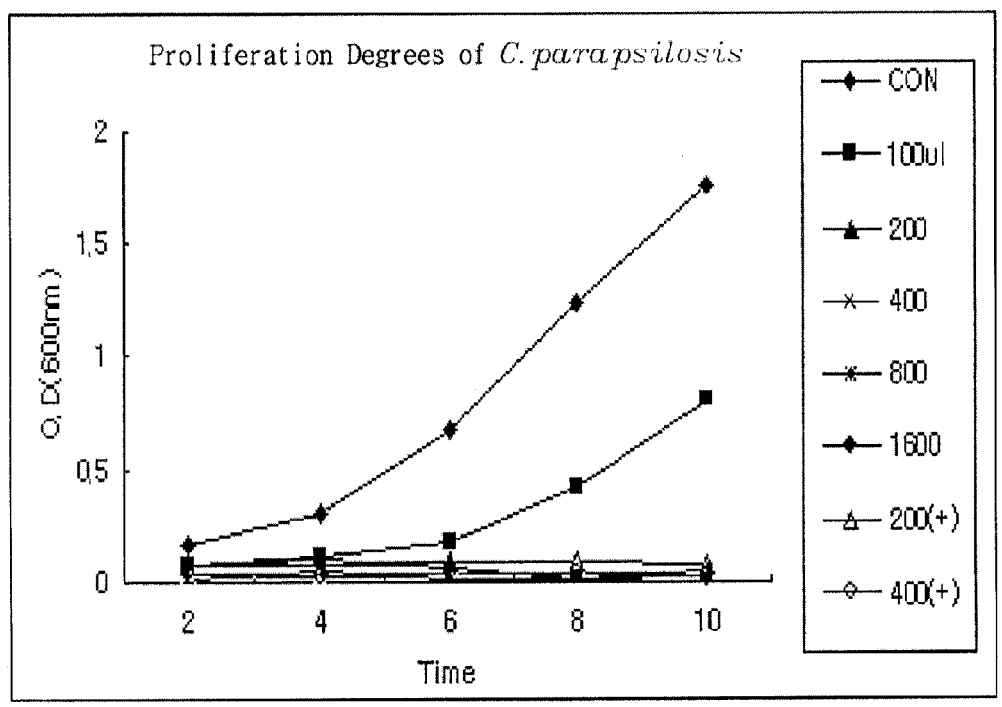

FIG. 5 shows proliferation degrees of *Candida parapsilosis* ATCC 22019 after treated with an oak extraction liquid and a silver-ionized oak extraction liquid. 'CON', '100', '200', '400', '800', '1600', '200(+)' and '400(+)' are the same as meant above.

Figure 6:
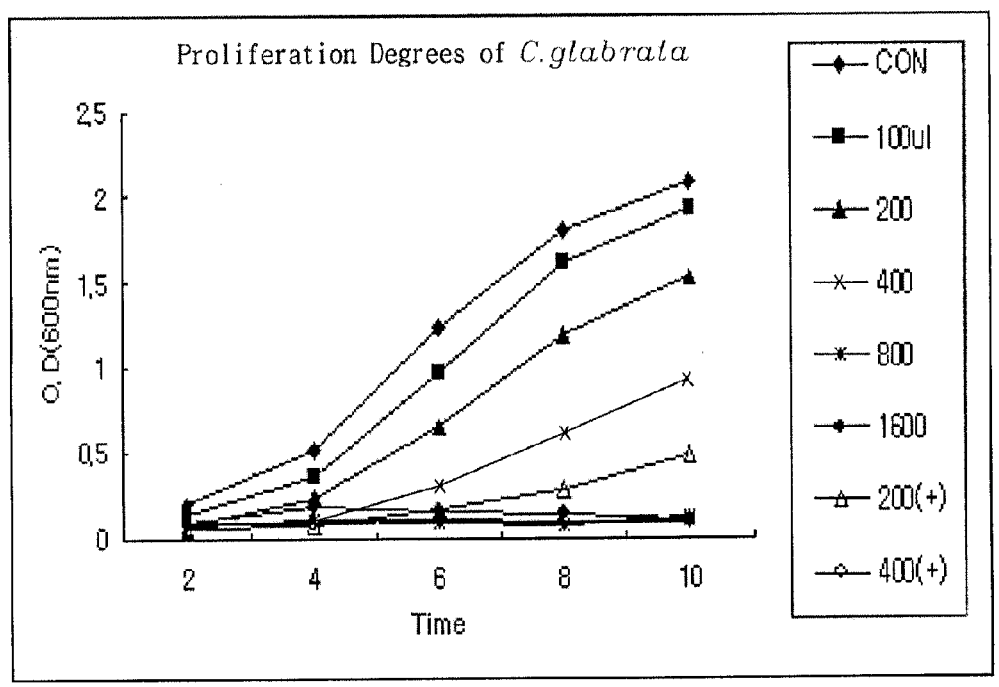

FIG. 6 shows proliferation degrees of *Candida glabrata* ATCC 90030 after treated with an oak extraction liquid and a silver-ionized oak extraction liquid. 'CON', '100', '200', '400', '800', '1600', '200(+)' and '400(+)' are the same as meant above.

Figure 7:
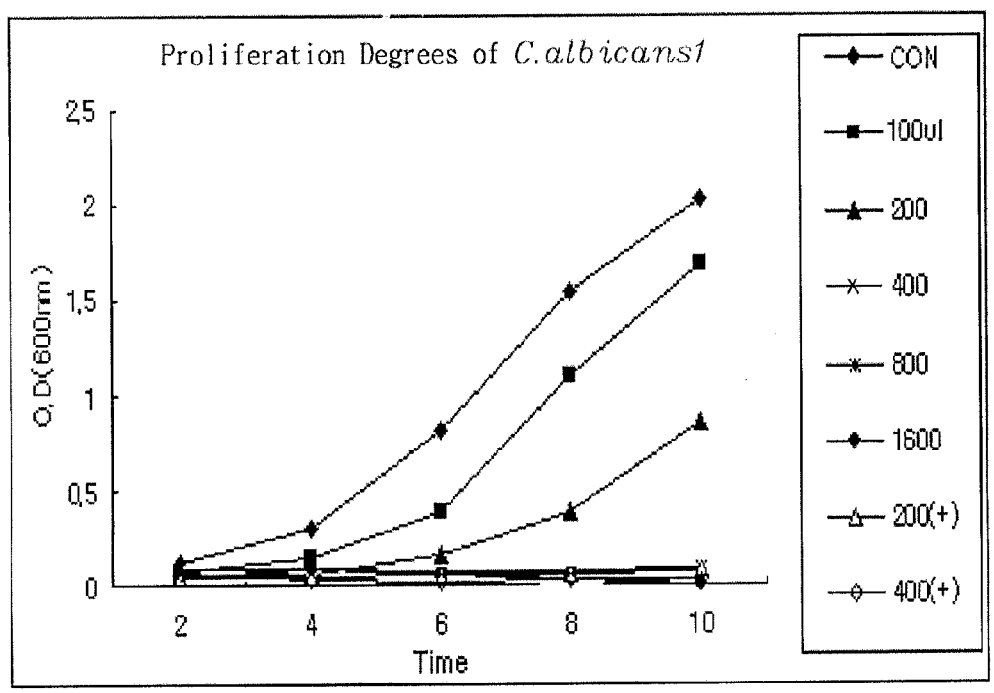

FIG. 7 shows proliferation degrees of *Candida albicans* ATCC 64550 after treated with an oak extraction liquid and a silver-ionized oak extraction liquid. 'CON', '100', '200', '400', '800', '1600', '200(+)' and '400(+)' are the same as meant above.

Figure 8:
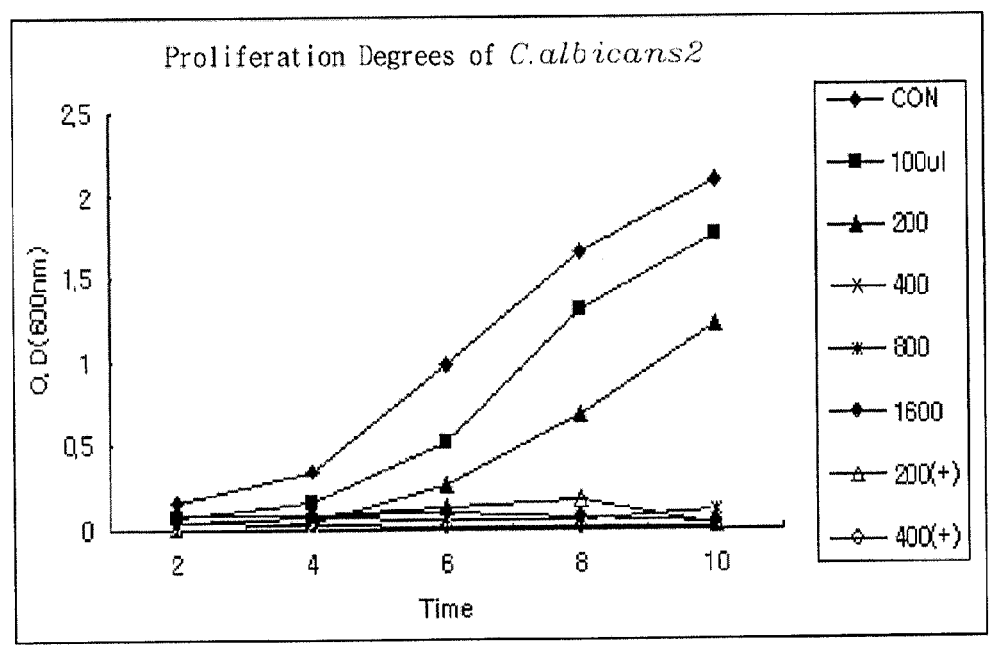

FIG. 8 shows proliferation degrees of *Candida albicans* ATCC 90028 after treated with an oak extraction liquid and a silver-ionized oak extraction liquid. 'CON', '100', '200', '400', '800', '1600', '200(+)' and '400(+)' are the same as meant above.

BEST MODE FOR INVENTION

The present invention is described more specifically by the following Examples. Examples herein are meant only to illustrate the present invention, but in no way to limit the claimed invention.

REFERENCE EXAMPLES

Preparation of Plant Extraction Liquid

Reference Example 1

Preparation of Bamboo Extraction Liquid

Bamboos were cut into pieces of about 30 cm and the middle parts of the pieces were heated up to 400° C. A bamboo extraction liquid was obtained by collecting resinous plant extraction liquid that flowed from the ends of the pieces. The bamboo extraction liquid was verified to have pH of 2.67.

Reference Example 2

Purchase of Oak Extraction Liquid

An oak extraction liquid (poroligenous liquor) was commercially purchased from Life-Chamsoot Corp. located at Seoul, Korea.

Reference Example 3

Preparation of Pine Extraction Liquid

Pine trees were cut into pieces of about 30 cm and the middle parts of the pieces were heated up to 300° C. A pine extraction liquid was obtained by collecting resinous plant extraction liquid that flowed from the ends of the pieces.

Reference Example 4

Preparation of *Thuja* Extraction Liquid

*Thuja* trees were cut into pieces of about 30 cm and the middle parts of the pieces were heated up to 400° C. A *thuja* extraction liquid was obtained by collecting resinous plant extraction liquid that flowed from the ends of the pieces.

Reference Example 5

Preparation of Marine Algae Extraction Liquid

A resinous marine algae extraction liquid, which was obtained by pressing marine algae, was commercially obtained from Freegrow, Harveson Inc. in Philippines (liquid phase, pH=14).

EXAMPLES

Preparation of Silver-Ionized Plant Extraction Liquid

Examples 1-10

Preparation of Silver-Ionized Bamboo Extraction Liquid by Electrolysis

The bamboo extraction liquid prepared in Reference Example 1 was placed in a non-conductive electrolytic bath, and two silver electrodes of high purity (>99.9%) were immersed in the extraction liquid. Ionization of silver was induced by connecting the electrodes to sources of electricity and applying a voltage for a predetermined time, as shown in Table 1. Dark brown precipitate was formed as result of a reaction between the silver ion and the bamboo extraction liquid, and totally removed by performing centrifuge and membrane filtration (Pall Corporation; Acrodisc Syringe Filter, 0.2 μm), thus a silver-ionized bamboo extraction liquid was finally prepared.

TABLE 1

| Examples | Voltage (V) | Time (minute) |
|---|---|---|
| Example 1 | 1.5 | 2 |
| Example 2 | 1.5 | 4 |
| Example 3 | 1.5 | 6 |
| Example 4 | 3 | 2 |
| Example 5 | 3 | 4 |
| Example 6 | 3 | 6 |
| Example 7 | 6 | 2 |
| Example 8 | 6 | 4 |
| Example 9 | 6 | 6 |
| Example 10 | 9 | 4 |

Examples 11-20

Preparation of Silver-Ionized Oak Extraction Liquid by Electrolysis

The oak extraction liquid prepared in Reference Example 2 was placed in a non-conductive electrolytic bath, and two silver electrodes of high purity (>99.9%) were immersed in the extraction liquid. Ionization of silver was induced by connecting the electrodes to sources of electricity and applying a voltage for a predetermined time as shown in Table 2. Dark brown precipitate was formed as result of a reaction between the silver ion and the oak extraction liquid, and totally removed by performing centrifuge and membrane filtration (Pall Corporation; Acrodisc Syringe Filter, 0.2 μm), thus a silver-ionized oak extraction liquid was finally prepared.

TABLE 2

| Examples | Voltage (V) | Time (minute) |
| --- | --- | --- |
| Example 11 | 1.5 | 2 |
| Example 12 | 1.5 | 4 |
| Example 13 | 1.5 | 6 |
| Example 14 | 3 | 2 |
| Example 15 | 3 | 4 |
| Example 16 | 3 | 6 |
| Example 17 | 6 | 2 |
| Example 18 | 6 | 4 |
| Example 19 | 6 | 6 |
| Example 20 | 9 | 4 |

Example 21

Preparation of Silver-Ionized Pine Extraction Liquid by Electrolysis

The pine extraction liquid prepared in Reference Example 3 was placed in a non-conductive electrolytic bath, and two silver electrodes of high purity (>99.9%) were immersed in the extraction liquid. Ionization of silver was induced by connecting the electrodes to sources of electricity and applying a voltage of 9 V for about 4 minutes. Dark brown precipitate was formed as result of a reaction between the silver ion and the pine extraction liquid, and totally removed by performing centrifuge and membrane filtration (Pall Corporation; Acrodisc Syringe Filter, 0.2 μm), thus a silver-ionized pine extraction liquid was finally prepared.

Example 22

Preparation of Silver-Ionized Thuja Extraction Liquid by Electrolysis

The thuja extraction liquid prepared in Reference Example 4 was placed in a non-conductive electrolytic bath, and two silver electrodes of high purity (>99.9%) were immersed in the extraction liquid. Ionization of silver was induced by connecting the electrodes to sources of electricity and applying a voltage of 9 V for 4 minutes. Dark brown precipitate was formed as result of a reaction between the silver ion and the thuja extraction liquid, and totally removed by performing centrifuge and membrane filtration (Pall Corporation; Acrodisc Syringe Filter, 0.2 μm), thus a silver-ionized thuja extraction liquid was finally prepared.

Example 23

Preparation of Silver-Ionized Marine Algae Extraction Liquid by Electrolysis

The marine algae extraction liquid prepared in Reference Example 4 was diluted two times with triple distilled water and upper solution was used as an electrolyte.

The upper solution was placed in a non-conductive electrolytic bath, and two silver electrodes of high purity (>99.9%) were immersed in the extraction liquid. Ionization of silver was induced by connecting the electrodes to sources of electricity and applying a voltage of 9 V for 4 minutes. Dark brown precipitate was formed as result of a reaction between the silver ion and the upper solution, and totally removed by performing centrifuge and membrane filtration (Pall Corporation; Acrodisc Syringe Filter, 0.2 μm), thus a silver-ionized marine algae extraction liquid was finally prepared.

EXPERIMENTAL EXAMPLES

Observation of Antimicrobial Activity

Experimental Example 1

Antimicrobial Activity of Silver-Ionized Bamboo Extraction Liquid (1-1) Antimicrobial Activity against *Candida* sp.

*Candida krusei* ATCC 6258, *Candida parapsilosis* ATCC 22019 and *Candida glabrata* ATCC 90030 were used herein as *Candida* sp.

Sterilized culture media (Sabouraud Dextrose Broth, 10 mL) was divided into 6 groups. One group was not treated at all and 4 groups were treated with 400 μL, 800 μL, 1,600 μL and 3,200 μL of the bamboo extraction liquid prepared in Reference Example 1, respectively. The other group was treated with 800 μL of silver-ionized bamboo extraction liquid prepared in Example 10. Each of the 6 groups was inoculated with 100 μL of fully-grown *Candida krusei* ATCC 6258, *Candida parapsilosis* ATCC 22019, *Candida glabrata* ATCC 90030, respectively, followed by cultivation at 30° C.

Figure 1:
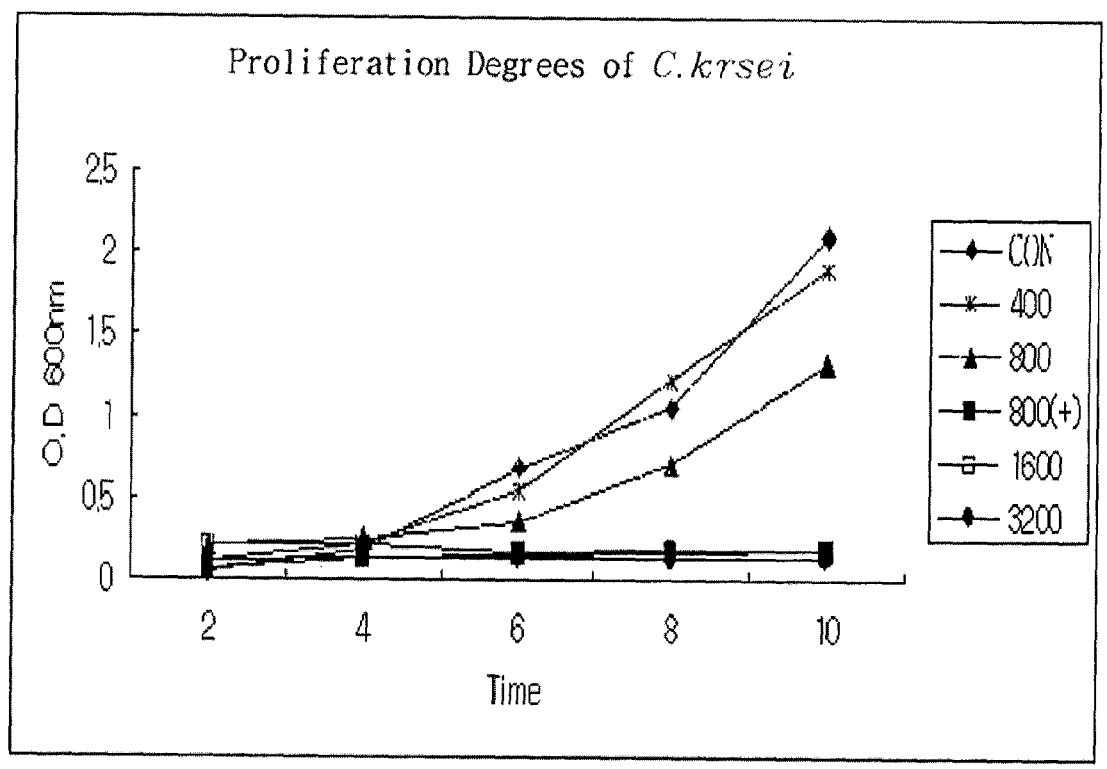
FIG. 1 shows proliferation degrees of *Candida krusei* ATCC 6258 after treated with a bamboo extraction liquid and a silver-ionized bamboo extraction liquid, respectively. 'CON' refers to non-treated group, and '400', '800', '1600' and '3200' refer to groups treated with 400 μL, 800 μL, 1600 μL and 3200 μL of a bamboo extraction liquid, '800(+)' represents a group treated with 800 μL of a silver-ionized bamboo extraction liquid.
Figure 2:
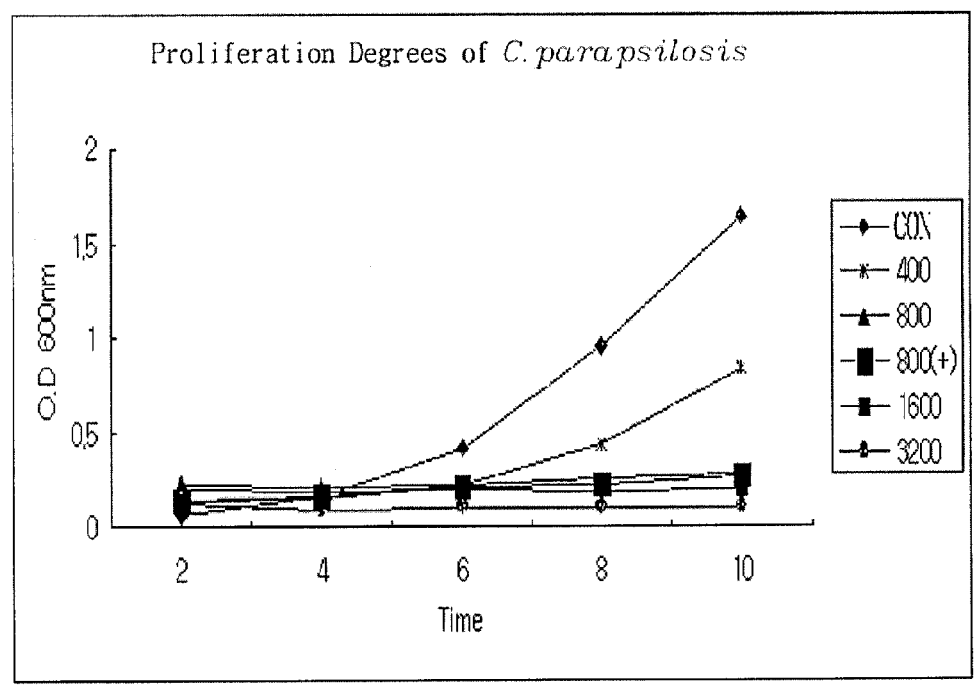
FIG. 2 shows proliferation degrees of *Candida parapsilosis* ATCC 22019 after treated with a bamboo extraction liquid and a silver-ionized bamboo extraction liquid. 'CON', '400', '800', '1600', '3200' and '800(+)' are the same as meant above.
Figure 3:
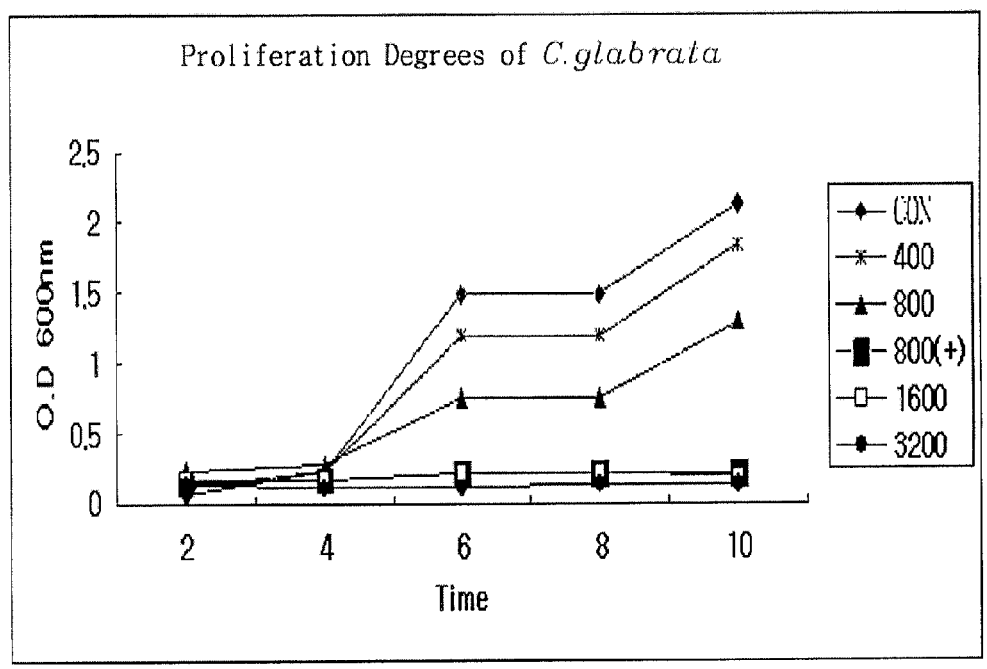
FIG. 3 shows proliferation degrees of *Candida glabrata* ATCC 90030 after treated with a bamboo extraction liquid and a silver-ionized bamboo extraction liquid. 'CON', '400', '800', '1600', '3200' and '800(+)' are the same as meant above.
Figure 4:
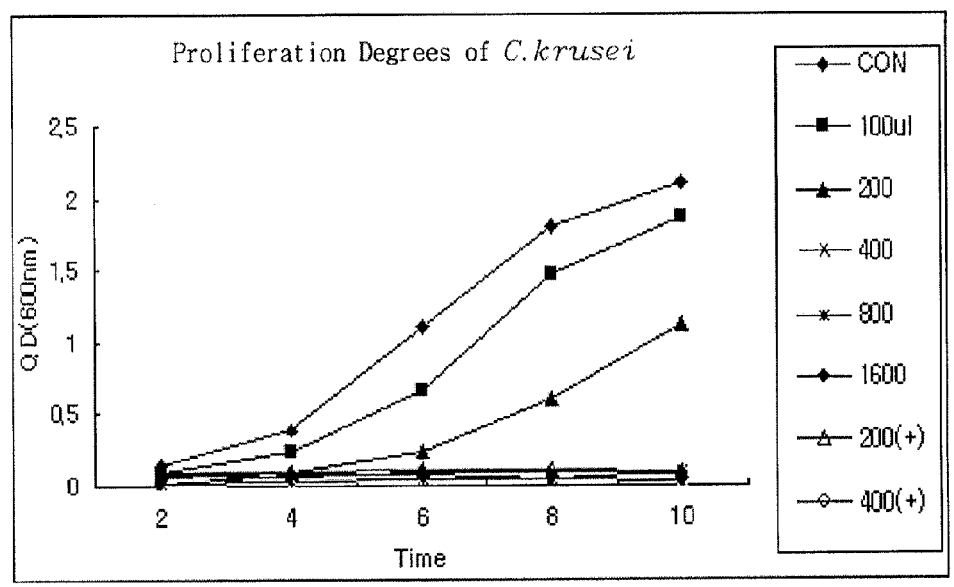
FIG. 4 shows proliferation degrees of *Candida krusei* ATCC 6258 after treated with an oak extraction liquid and a silver-ionized oak extraction liquid. 'CON' refers to non-treated group, and '100', '200', '400', '800' and '1600' refer to groups treated with 100 μL, 200 μL, 400 μL, 800 μL and 1600 μL of an oak extraction liquid. '200(+)' and '400(+)' represent groups treated with 200 μL and 400 μL of a silver-ionized oak extraction liquid, respectively.

During cultivation, O.D. values were measured at an interval of 2 hours and the results of strain growth were shown in FIGS. 1-3, which represent *Candida krusei* ATCC 6258, *Candida parapsilosis* ATCC 22019 and *Candida glabrata* ATCC 90030, respectively.

In the case of *Candida krusei*, the bamboo extraction liquid prepared in Reference Example 1 did not affect in an amount of 400 μL and began to show an antimicrobial activity in an amount of 800 μL. The growth of *Candida krusei* was totally inhibited by the addition of 1600 μL of the bamboo extraction liquid. The inhibition was also accomplished by the addition of 800 μL, of silver-ionized bamboo extraction liquid. These results show that MIC (minimum inhibitory concentration) value of the bamboo extraction liquid is higher than 800 μL/mL while MIC value of the silver-ionized bamboo extraction liquid is lower than 800 μL/mL.

Growth of *Candida parapsilosis* was totally inhibited either by the addition of 800 μL of the bamboo extraction liquid or by the addition of 800 μL of the silver-ionized bamboo extraction liquid. *Candida glabrata* was similar to the case of *Candida krusei* in growth inhibition, which was accomplished by the addition of 1600 μL of the bamboo extraction liquid and by addition of 800 μL of the silver-ionized bamboo extraction liquid respectively.

(1-2) Antimicrobial Activity against Bacteria and Yeast

Among bacteria, *E. coli* 0157 KCCM 40406, *Bacillus therengenesis* KCTC 1034, *Staphylococcus warneri* KACC 10785, *Staphylococcus aureus* KACC 10778, *Staphylococcus aureus* KACC 10778 and *Vibrio* sp. (available from Chon-nam national university hospital in Korea) were initially grown in LB Broth (37° C., 12 hours). *Aeromonas hydrophila* subsp. *Hydrophila* KCCM 32586 and *Chromobacterium violaceum* KCCM 11748 were initially grown in nutrient Broth media (26° C., 18 hours). *Streptococcus pyogenes* KCCM 11856 and *Streptococcus mutants* KCCM 40105 were initially grown in BHI (Brain Heart Infusion) Broth media (37° C., 18 hours). *Lactobacillus crispatus* KCCM 41620 and *Candida* sp. was initially grown in Lactobacilli MRS Broth media (37° C., 18 hours) and SD (Sabouraud Dextrose) Broth (30° C., 12 hours), respectively.

100 μL of the cultivated strain was inoculated to each Petri dish containing LB agar. 12 μL of the bamboo extraction liquid (Reference Example 1), the silver-ionized water and the silver-ionized bamboo extraction liquid (Example 10)

were added to the inoculated medium, followed by culture at constant-temperature bath for 12 hours. It was determined by using clear zone whether the bacteria grew or not, and the results are provided in Table 3.

The silver-ionized water was prepared by means of electrolysis in the same conditions as set forth in Example 10 except using triple distilled water instead of the bamboo extraction liquid of Reference Example 1.

TABLE 3

| Strain | Bamboo extraction liquid | Silver-ionized water | Silver-ionized bamboo extraction liquid |
|---|---|---|---|
| E. coli 0157 KCCM 40406 | ** | — | *** |
| Salmonella choeraesuis KCCM 41038 | ** | — | *** |
| Bacillus therengenesis KCTC 1034 | * | — | *** |
| Staphylococcus warneri KACC 10785 | * | — | *** |
| Staphylococcus aureus KACC 10778 | — | — | *** |
| Vibrio sp.(Chon-nam national Univ.) | — | — | ** |
| Aeromonas hydrophila subsp. Hydrophila KCCM 32586 | *** | — | *** |
| Chromobacterium violaceum KCCM 11748 | *** | — | *** |
| Streptococcus pyogenes KCCM 11856 | — | — | *** |
| Streptococcus mutants KCCM 40105 | * | — | *** |
| Lactobacillus crispatus KCCM 41620 | — | — | *** |
| Candida parapsilosis ATCC 22019 | — | — | ** |
| Candida glabrata ATCC 90030 | — | — | ** |
| Candida krusei ATCC 6258 | — | — | *** |
| Candida albicans 1 ATCC 64550 | — | — | ** |
| Candida albicans 2 ATCC 90028 | — | — | ** |

— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 3 shows a synergistic antimicrobial activity of the silver-ionized bamboo extraction liquid prepared in Example 10 as compared to the bamboo extraction liquid and the silver-ionized water. The reason why the silver-ionized water showed no antimicrobial activity is assumed to be that the voltage was low and the time was short during electrolysis.

(1-3) Antimicrobial activity Against Fungi

Aspergillus ocnraceus KACC 4007, Trichoderma harzianum KCTC 6426, Fusarium solani KCTC 6328 and Fusarium oxysporum KACC 40037 were grown in PDA (Potato Dextrose Agar, Duchefa) media. Aspergillus ochraceus KACC 40077, Fusarium solani KACC 40384 and Fusarium graminearum KACC 40532 were grown in MEA (Malt Extraction liquid Agar) media. Trichophyton rubrum KCTC 6345, Microsporum audouinii KCTC 6346 and Trichophyton ferrugineum KCTC 6351 were grown in SDA (Sabouraud Dextrose Agar) media. The microorganisms were inoculated into the center of the media and allowed to begin in vitro vegetative propagation of a circle shape. After about 7 days, about 300 μL, of each reagent, i.e. the bamboo extraction liquid (Reference Example 1), the silver-ionized water, the silver-ionized bamboo extraction liquid (Example 10), was absorbed into each of paper disks at a constant distance. It was observed whether the microorganisms proliferated into the reagent-treated regions after 12 hours, and the results are provided in Table 3.

The silver-ionized water was prepared by means of electrolysis in the same conditions as set forth in Example 10 except using triple distilled water instead of the bamboo extraction liquid of Reference Example 1.

TABLE 4

| Strain | Bamboo extraction liquid | Silver-ionized water | Silver-ionized bamboo extraction liquid |
|---|---|---|---|
| Aspergillus ocnraceus KACC 4007 | * | — | ** |
| Trichoderma harzianum KCTC 6426 | * | — | ** |
| Fusarium solani KCTC 6328 | * | — | ** |
| Fusarium oxysporum KACC 40037 | ** | — | *** |
| Aspergillus ochraceus (KACC 40077) | — | — | *** |
| Fusarium solani (KACC 40384) | * | — | *** |
| Fusarium graminearum (KACC 40532) | — | — | ** |
| Trichophyton rubrum KCTC 6345 | * | — | *** |
| Microsporum audouinii KCTC 6346 | — | — | *** |
| Trichophyton ferrugineum KCTC 6351 | * | — | *** |

— No antimicrobial activity
* Proliferation beyond the line of the reagent-treated paper disk was observed.
** Proliferation in the form of a concentric circle with radiation of 0.5 cm greater than the reagent-treated paper disk was observed.
*** Proliferation in the form of a concentric circle with radiation of 1 cm greater than the reagent-treated paper disk was observed.

Table 4 also shows a synergistic antimicrobial activity of the silver-ionized bamboo extraction liquid prepared in Example 10 as compared to the bamboo extraction liquid and the silver-ionized water. The reason why the silver-ionized water showed no antimicrobial activity is assumed to be the same as set forth in Table 3.

(1-4) Effect of Electrolysis Voltage and Time on Antimicrobial Activity

It was observed the degree to which the voltage and time of electrolysis affect an antimicrobial activity of the silver-ionized bamboo extraction liquid by using the silver-ionized bamboo extraction liquid prepared in each of Examples 1-10. The experimental process was the same as Experimental Example 1-2 right above, and the results are provided in Table 5.

TABLE 5

| Examples | 1 | 2 | 3 | 4 | 5 | 6 | 7 | 8 | 9 | 10 |
|---|---|---|---|---|---|---|---|---|---|---|
| Example 1 | *** | *** | * | — | — | — | — | — | — | * |
| Example 2 | *** | *** | * | — | * | * | — | — | — | ** |
| Example 3 | *** | *** | * | — | *** | * | — | — | — | ** |
| Example 4 | *** | *** | ** | ** | ** | * | — | — | * | — |
| Example 5 | *** | *** | ** | ** | *** | ** | — | * | *** | * |
| Example 6 | *** | *** | *** | *** | *** | ** | — | *** | *** | ** |
| Example 7 | *** | *** | *** | *** | *** | ** | * | *** | ** | *** |

TABLE 5-continued

| Examples | 1 | 2 | 3 | 4 | 5 | 6 | 7 | 8 | 9 | 10 |
|---|---|---|---|---|---|---|---|---|---|---|
| Example 8 | *** | *** | *** | *** | *** | *** | ** | *** | *** | *** |
| Example 9 | *** | *** | *** | *** | *** | *** | *** | *** | *** | *** |

1: *E. coli* 0157 KCCM 40406
2: *Salmonella choeraesuis* KCCM 41038
3: *Bacillus therengenesis* KCTC 1034
4: *Staphylococcus warneri* KACC 10785
5: *Staphylococcus aureus* KACC 10778
6: *Candida parapsilosis* ATCC 22019
7: *Candida glabrata* ATCC90030
8: *Candida krusei* ATCC 6258
9: *Candida albicans* 1 ATCC 64550
10: *Candida albicans* 2 ATCC 90028
— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 5 shows that higher voltage and longer time of electrolysis causes higher antimicrobial activity of the silver-ionized bamboo extraction liquid.

Experimental Example 2

Antimicrobial Activity of Silver-Ionized Oak Extraction Liquid (2-1) Antimicrobial Activity against *Candida* sp.
According to process similar to that in Experimental Example 1-1, an antimicrobial activity against *Candida* sp. was observed.

As *Candida* sp., *Candida krusei* ATCC 6258, *Candida parapsilosis* ATCC 22019, *Candida glabrata* ATCC 90030, *Candida albicans* ATCC 64550 and *Candida albicans* ATCC 90028 were used herein.

Sterilized culture media (Sabouraud Dextrose Broth) was divided into 8 groups. One group was not treated (CON), and 5 groups were treated with 100 μL, 200 μL, 400 μL, 800 μL and 1,600 μL of the oak extraction liquid prepared in Reference Example 2, respectively. The other 2 groups were treated with 200 μL and 400 μL of the silver-ionized oak extraction liquid prepared in Example 20. Each of the 8 groups was inoculated with 100 μL of fully-grown *Candida krusei* ATCC 6258, *Candida parapsilosis* ATCC 22019, *Candida glabrata* ATCC 90030, *Candida albicans* ATCC 64550(*C. albicans* 1) and *Candida albicans* ATCC 90028 (*C. albicans* 2), respectively, followed by cultivation at 30° C.

During cultivation, O.D. values (600 nm) were measured at an interval of 2 hours and the results of strain growth were shown in FIGS. 4-8, which represent *Candida Candida krusei* ATCC 6258, *Candida parapsilosis* ATCC 22019, *Candida glabrata* ATCC 90030, *Candida albicans* ATCC 64550 and *Candida albicans* ATCC 90028, respectively.

In the case of *Candida krusei* and two kinds of *Candida albicans*, the oak extraction liquid prepared in Reference Example 2 did not affect in an amount of 100 μL and began to show an antimicrobial activity in an amount of 200 μL. The growth was totally inhibited by the addition of 400 μL of the oak extraction liquid. The inhibition was also accomplished by the addition of 200 μL of the silver-ionized oak extraction liquid. These results show that MIC (minimum inhibitory concentration) value of the oak extraction liquid is above 200 μL/mL while MIC value of the silver-ionized oak extraction liquid is lower than 200 μL/mL.

Growth of *Candida parapsilosis* was totally inhibited either by the addition of 200 μL of the oak extraction liquid or by the addition of 200 μL of the silver-ionized oak extraction liquid. *Candida glabrata* was similar to the case of *Candida krusei* in growth inhibition, which was accomplished by the addition of 800 μL of the oak extraction liquid and by addition of 400 μL of the silver-ionized oak extraction liquid respectively.

(2-2) Antimicrobial Activity against Bacteria and Yeast
According to process similar to that in Experimental Example 1-2, an antimicrobial activity against bacteria and yeast was observed.

Bacteria were initially grown in LB Broth (37° C., 12 hours) and *Candida* sp. was initially grown in SD (Sabouraud Dextrose) Broth (30° C., 12 hours).

100 μL of the cultivated strain was inoculated to each Petri dish containing LB agar. 12 μL of the oak extraction liquid (Reference Example 2), the silver-ionized water and the silver-ionized oak extraction liquid (Example 20) were added to the inoculated medium, followed by culture at constant-temperature bath for 12 hours. It was determined by using clear zone whether the bacteria grew or not, and the results are provided in Table 6.

The silver-ionized water was prepared by means of electrolysis in the same conditions as set forth in Example 20 except using triple distilled water instead of the oak extraction liquid of Reference Example 2.

TABLE 6

| Strain | Oak extraction liquid | Silver-ionized water | Silver-ionized oak extraction liquid |
|---|---|---|---|
| *E. coli* 0157 KCCM 40406 | ** | — | *** |
| *Salmonella choeraesuis* KCCM 41038 | ** | — | *** |
| *Bacillus therengenesis* KCTC 1034 | ** | — | *** |
| *Staphylococcus warneri* KACC 10785 | ** | — | *** |
| *Staphylococcus aureus* KACC 10778 | — | — | *** |
| *Vibrio* sp. (Chon-nam national univ.) | — | — | ** |
| *Candida parapsilosis* ATCC 22019 | — | — | ** |
| *Candida glabrata* ATCC90030 | — | — | ** |
| *Candida krusei* ATCC 6258 | — | — | *** |
| *Candida albicans* 1 ATCC 64550 | — | — | ** |
| *Candida albicans* 2 ATCC 90028 | — | — | ** |

— Low antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 6 shows a synergistic antimicrobial activity of the silver-ionized oak extraction liquid prepared in Example 20 as compared to the oak extraction liquid and the silver-ionized water. The reason why the silver-ionized water showed no antimicrobial activity is assumed to be the same as set forth above.

(2-3) Antimicrobial Activity against Fungi

According to process similar to that in Experimental Example 1-3, an antimicrobial activity against fungi was observed.

Microorganisms were inoculated into the center of the media (Potato Dextrose Agar/Duchefa) and allowed to begin in vitro vegetative propagation of a circle shape. After about 7 days, about 25 μL of each reagent, i.e. the oak extraction liquid (Reference Example 2), the silver-ionized water, the silver-ionized oak extraction liquid (Example 20), was absorbed into paper disk at a constant distance. It was observed whether the microorganisms proliferated into the reagent-treated regions after 12 hours, and the results are provided in Table 7.

The silver-ionized water was prepared by means of electrolysis in the same conditions as set forth in Example 20 except using triple distilled water instead of the oak extraction liquid of Reference Example 2.

TABLE 7

| Strain | Oak extraction liquid | Silver-ionized water | Silver-ionized oak extraction liquid |
|---|---|---|---|
| Aspergillus ocnraceus KACC 4007 | ** | — | ** |
| Trichoderma harzianum KCTC 6426 | * | — | ** |
| Fusarium solani KCTC 6328 | ** | — | ** |
| S Fusarium oxysporum KACC 40037 | ** | — | *** |

— No antimicrobial activity
* Proliferation beyond the line of the reagent-treated paper disk was observed.
** Proliferation in the form of a concentric circle with radiation of 0.5 cm greater than the reagent-treated paper disk was observed.
*** Proliferation in the form of a concentric circle with radiation of 1 cm greater than the reagent-treated paper disk was observed.

Table 7 also shows a synergistic antimicrobial activity of the silver-ionized oak extraction liquid prepared in Example 20 as compared to the oak extraction liquid and the silver-ionized water. The reason why the silver-ionized water showed no antimicrobial activity is assumed to be the same as set forth in Table 3.

(2-4) Effect of Electrolysis Voltage and Time on Antimicrobial Activity

It was observed the degree to which the voltage and time of electrolysis affect an antimicrobial activity by using the silver-ionized oak extraction liquid prepared in each of Examples 11-20. The experimental process was the same as Experimental Example 2-2 right above, and the results are provided in Table 8.

TABLE 8

| Strain | 11 | 12 | 13 | 14 | 15 | 16 | 17 | 18 | 19 | 20 |
|---|---|---|---|---|---|---|---|---|---|---|
| Example 1 | *** | *** | * | — | — | — | — | — | — | * |
| Example 2 | *** | *** | * | — | * | * | — | — | — | ** |
| Example 3 | *** | *** | * | — | *** | * | — | — | — | ** |
| Example 4 | *** | *** | ** | ** | ** | * | — | — | * | — |
| Example 5 | *** | *** | ** | ** | *** | ** | — | * | *** | * |
| Example 6 | *** | *** | *** | *** | *** | ** | — | *** | *** | ** |
| Example 7 | *** | *** | *** | *** | *** | ** | * | *** | ** | *** |
| Example 8 | *** | *** | *** | *** | *** | *** | ** | *** | *** | *** |
| Example 9 | *** | *** | *** | *** | *** | *** | *** | *** | *** | *** |

1: *E. coli* 0157 KCCM 40406
2: *Salmonella choeraesuis* KCCM 41038
3: *Bacillus therengenesis* KCTC 1034
4: *Staphylococcus warneri* KACC 10785
5: *Staphylococcus aureus* KACC 10778
6: *Candida parapsilosis* ATCC 22019
7: *Candida glabrata* ATCC90030
8: *Candida krusei* ATCC 6258
9: *Candida albicans* 1 ATCC 64550
10: *Candida albicans* 2 ATCC 90028
— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 8 also shows that higher voltage and longer time of electrolysis causes higher antimicrobial activity of the silver-ionized oak extraction liquid.

Experimental Example 3

Antimicrobial Activity of Silver-Ionized Pine Extraction Liquid

According to process similar to that in Experimental Example 1-2, an antimicrobial activity against bacteria and yeast was observed.

Bacteria was initially grown in MH (Mueller Hinton) Broth (37° C., 12 hours) and *Candida* sp. was initially grown in SD (Sabouraud Dextrose) Broth (30° C., 12 hours). 100 μL, of the cultivated strain was inoculated to each Petri dish containing MH agar. 15 μL of the pine extraction liquid (Reference Example 3), the silver-ionized water and the silver-ionized pine extraction liquid (Example 21) were added to the inoculated medium, followed by culture at constant-temperature bath for 12 hours. It was determined by using clear zone whether the bacteria grew or not, and the results are provided in Table 9.

The silver-ionized water was prepared by means of electrolysis in the same conditions as set forth in Example 21 except using triple distilled water instead of the oak extraction liquid of Reference Example 3.

TABLE 9

| Strain | Pine extraction liquid | Silver-ionized water | Silver-ionized pine extraction liquid |
|---|---|---|---|
| E. coli 0157 KCCM 40406 | — | — | *** |
| Salmonella choleraesuis KCCM 41038 | — | — | *** |
| Bacillus therengenesis KCTC 1034 | — | — | *** |
| Staphylococcus epidermidis (LG Chem, Ltd.) | — | — | *** |
| Staphylococcus aureus (LG Chem, Ltd.) | — | — | *** |
| Serratia marcescens (LG Chem, Ltd.) | — | — | *** |
| Candida albicans 1 ATCC 64550 | — | — | * |

— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 9 also shows a synergistic antimicrobial activity of the silver-ionized pine extraction liquid prepared in Example 20 as compared to the pine extraction liquid and the silver-ionized water. The reason why the silver-ionized water showed no antimicrobial activity is assumed to be the same as set forth in Table 3.

Experimental Example 4

Antimicrobial Activity of Silver-Ionized *Thuja* Extraction Liquid

According to process similar to that in Experimental Example 1-2, an antimicrobial activity against bacteria and yeast was observed.

Bacteria was initially grown in MH (Mueller Hinton) Broth (37° C., 12 hours) and *Candida* sp. was initially grown in SD (Sabouraud Dextrose) Broth (30° C., 12 hours). 100 μL of the cultivated strain was inoculated to each Petri dish containing MH agar. 15 μL of the *thuja* extraction liquid (Reference Example 4), the silver-ionized water and the silver-ionized *thuja* extraction liquid (Example 22) were added to the inoculated medium, followed by culture at constant-temperature bath for 12 hours. It was determined by using clear zone whether the bacteria grew or not, and the results are provided in Table 10.

The silver-ionized water was prepared by means of electrolysis in the same conditions as set forth in Example 22 except using triple distilled water instead of the *thuja* extraction liquid of Reference Example 4.

TABLE 10

| Strain | Thuja extraction liquid | Silver-ionized water | Silver-ionized thuja extraction liquid |
|---|---|---|---|
| E. coli 0157 KCCM 40406 | — | — | *** |
| Salmonella choleraesuis KCCM 41038 | * | — | *** |
| Bacillus therengenesis KCTC 1034 | — | — | *** |
| Staphylococcus epidermidis (LG Chem, Ltd.) | * | — | *** |
| Staphylococcus aureus (LG Chem, Ltd.) | — | — | *** |
| Serratia marcescens (LG Chem, Ltd.) | * | — | *** |
| Candida albicans 1 ATCC 64550 | — | — | *** |

— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 10 also shows a synergistic antimicrobial activity of the silver-ionized *thuja* extraction liquid prepared in Example 22 as compared to the *thuja* extraction liquid and the silver-ionized water. The reason why the silver-ionized water showed no antimicrobial activity is assumed to be the same as set forth in Table 3.

Experimental Example 5

Antimicrobial Activity of Silver-Ionized Marine Algae Extraction Liquid

According to process similar to that in Experimental Example 1-2, an antimicrobial activity against bacteria and yeast was observed.

Bacteria was initially grown in MH (Mueller Hinton) Broth (37° C., 12 hours) and *Candida* sp. was initially grown in SD (Sabouraud Dextrose) Broth (30° C., 12 hours). 100 μL of the cultivated strain was inoculated to each Petri dish containing MH agar. 15 μL of the marine algae extraction liquid (Reference Example 5), the silver-ionized water and the silver-ionized marine algae extraction liquid (Example 23) were added to the inoculated medium, followed by culture at constant-temperature bath for 12 hours. It was determined by using clear zone whether the bacteria grew or not, and the results are provided in Table 11.

The silver-ionized water was prepared by means of electrolysis in the same conditions as set forth in Example 23 except using triple distilled water instead of the marine algae extraction liquid of Reference Example 5.

TABLE 11

| Strain | Marine algae extraction liquid | Silver-ionized water | Silver-ionized marine algae extraction liquid |
|---|---|---|---|
| E. coli 0157 KCCM 40406 | ** | — | *** |
| Salmonella choleraesuis KCCM 41038 | ** | — | *** |
| Bacillus therengenesis KCTC 1034 | — | — | *** |
| Staphylococcus epidermidis (LG Chem, Ltd.) | * | — | *** |
| Staphylococcus aureus (LG Chem, Ltd.) | — | — | ** |
| Serratia marcescens (LG Chem, Ltd.) | * | — | *** |

TABLE 11-continued

| Strain | Marine algae extraction liquid | Silver-ionized water | Silver-ionized marine algae extraction liquid |
|---|---|---|---|
| Candida albicans 1 ATCC 64550 | — | — | *** |

— No antimicrobial activity
* Small clear zone, small amount of microorganisms in zone and proliferation of the microorganisms was observed after 24 hours.
** Small clear zone, very small amount of microorganisms in zone and proliferation of the microorganisms was observed after 48 hours.
*** Large clear zone, no microorganism in zone and proliferation of the microorganisms was observed after 48 hours.

Table 11 also shows a synergistic antimicrobial activity of the silver-ionized marine algae extraction liquid prepared in Example 23 as compared to the marine algae extraction liquid and the silver-ionized water. The reason why the silver-ionized water showed no antimicrobial activity is assumed to be the same as set forth in Table 3.

It seems that the synergistic antimicrobial activity of the silver-ionized plant extraction liquid herein is based on an unknown material that is assumed to be prepared by the reaction of the silver ion with the plant extraction liquid. Meanwhile, although it was not disclosed above, the silver-ionized bamboo or oak extraction liquid was also verified to be antimicrobial activity against *Bacillus anthracis, E. coli* DH 5α, *Staphylococcus schleiferi*.

REFERENCES

The below-mentioned papers are incorporated by reference herein in their entirety for better understanding the level of related arts and the gist of the present invention.

1. Ripeau J S, Aumont F, Belhumeur P, Ostrosky-Zeichner L, Rex J H, de Repentigny L. Effect of the echinocandin caspofungin on expression of *Candida albicans* secretory aspartyl proteinases and phospholipase in vitro. Antimicrob Agents Chemother. 2002 September; 46(9):3096-100
2. Barousse, M. M., C. Steele, K. Dunlap, T. Espinosa, D. Boikov, J. D. Sobel, and P. L. Fidel, Jr. 2001. Growth inhibition of *Candida albicans* by human vaginal epithelial cells. J. Infect. Dis. 184:1489-1493.
3. Brassart, D., A. Woltz, M. Golliard, and J. R. Neeser. 1991. In vitro inhibition of adhesion of *Candida albicans* clinical isolates to human buccal epithelial cells by Fuc 132Gal-bearing complex carbohydrates. Infect. Immun. 59:1605-1613.
4. Cameron, B. J., and L. J. Douglas. 1996. Blood group glycolipids as epithelial cell receptors for *Candida albicans*. Infect. Immun. 64:891-896.
5. Chaim, W., B. Foxman, and J. D. Sobel. 1997. Association of recurrent vaginal candidiasis and secretory ABO and Lewis phenotype. J. Infect. Dis. 176:828-830.
6. Critchley, I. A., and L. J. Douglas. 1987. Role of glycosides as epithelial cell receptors for *Candida albicans*. J. Gen. Microbiol. 133:637-643.
7. Fidel, P. L., Jr. 2002. Immunity to *Candida*. Oral Dis. 8(Suppl. 2):69-75.
8. Fidel, P. L., Jr., J. Cutright, and C. Steele. 2000. Effects of reproductive hormones on experimental vaginal candidiasis. Infect. Immun. 68:651-657.
9. Fidel, P. L., Jr., M. E. Lynch, and J. D. Sobel. 1993. *Candida*-specific cellmediated immunity is demonstrable in mice with experimental vaginal candidiasis. Infect. Immun. 61:1990-1995.
10. Han, Y., R. P. Morrison, and J. E. Cutler. 1998. A vaccine and monoclonal antibodies that enhance mouse resistance to *Candida albicans* vaginal infection. Infect. Immun. 66:5771-5776.
11. Kelly, R. J., S. Rouquier, D. Giorgi, G. G. Lennon, and J. B. Lowe. 1995. Sequence and expression of a candidate for the human secretor blood group (1,2)fucosyltransferase gene (FUT2). Homozygosity for an enzyme-inactivating nonsense mutation commonly correlates with the nonsecretor phenotype. J. Biol. Chem. 270:4640-4649.
12. Kirkpatrick W R, Lopez-Ribot J L, McAtee R K, Patterson T F Growth competition between *Candida dubliniensis* and *Candida albicans* under broth and biofilm growing conditions. Clin Microbiol. 2000 February; 38(2):902-4.
13. Schaeffer, A. J., N. Rajan, Q. Cao, B. E. Anderson, D. L. Pruden, J. Sensibar, and J. L. Duncan. 2001. Host pathogenesis in urinary tract infections. Int. J. Antimicrob. Agents 17:245-251.
14. Sobel, J. D. 1988. Pathogenesis and epidemiology of vulvovaginal candidiasis. Ann. N. Y. Acad. Sci. 544:547-557.
15. Sobel, J. D. 1992. Pathogenesis and treatment of recurrent vulvovaginal candidiasis. Clin. Infect. Dis. 14(Suppl. 1):S148-S153.
16. Steele, C., J. Leigh, R. Swoboda, H. Ozenci, and P. L. Fidel, Jr. 2001. Potential role for a carbohydrate moiety in anti-Candida activity of human oral epithelial cells. Infect. Immun. 69:7091-7099.
17. Vardar-Unlu, G., C. McSharry, and L. J. Douglas. 1998. Fucose-specific adhesins on germ tubes of *Candida albicans*. FEMS Immunol. Med. Microbiol. 20:55-67.
18. Kirkpatrick W R, Lopez-Ribot J L, McAtee R K, Patterson T F Growth competition between *Candida dubliniensis* and *Candida albicans* under broth and biofilm growing conditions. Clin Microbiol. 2000 February; 38(2):902-4.
19. Saadi, A. T., D. M. Weir, I. R. Poxton, J. Stewart, S. D. Essery, C. C. Blackwell, M. W. Raza, and A. Busuttil. 1994. Isolation of an adhesin from *Staphylococcus aureus* that binds Lewis a blood group antigen and its relevance to sudden infant death syndrome. FEMS Immunol. Med. Microbiol. 8:315-320.
20. Steinberg, J. P., Clark, C. C., and Hackman, B. O. 1996. Nosocomial and community-acquired *Staphylococcus aureus* bacteremias from 1980 to 1993: impact of intravascular devices and methicillin resistance. Clin. Infect. Dis. 23:255.259.
21. *Staphylococcus* Laboratory, Statens Serum Institut. 2003. Annual report on *Staphylococcus aureus* bacteraemia cases 2001. *Staphylococcus* Laboratory, National Center for Antimicrobials and Infection Control, Statens Serum Institut. Copenhagen, Denmark. 9 pp.
22. Luzar, M. A., et al. 1990. *Staphylococcus aureus* nasal carriage and infection in patients on continuous ambulatory peritoneal dialysis. N. Engl. J. Med. 322:505.509.
23. Yu, V. L., et al. 1986. *Staphylococcus aureus* nasal carriage and infection in patients on hemodialysis. Efficacy of antibiotic prophylaxis. N. Engl. J. Med. 315:91.96.
24. Nguyen, M. H., et al. 1999. Nasal carriage of and infection with *Staphylococcus aureus* in HIV-infected patients. Ann. Intern. Med. 130:221.225.
25. Moss, B., Squire, J. R., and Topley, E. 1948. Nose and skin carriage of *Staphylococcus aureus* in patients receiving penicillin. Lancet. 1:320.325.
26. Sherman P, Drumm B, Karmali M & Cutz E. Adherence of bacteria to the intestine in sporadic cases of Enteropathogenic *Escherichia coli*-associated diarrhea in infants and young children: a prospective study. Gastroenterol, 1989; 96:86:-94
27. Cravioto A, Gross R J, Scotland S M, Rowe B. An adhesive factor found in strains of *escherichia coli* belonging to the traditional infantile enteropathogenic serotypes. Current Microbiology,1979; 3:95-9.
28. Scaletsky I C A, Silva M L M, Trabulsi L R. Distinctive patterns of adherence of enteropathogenic *Escherichia coli* to HelLa cells. Infct. Immun., 1984; 45:534-6.
29. Nataro J P, Baldini M M, Kaper J B, Black R E, Bravo N, Levine M. M. Detection of an adherence factor of enteropathogenic *Escherichia coli* with a DNA probe. Infect. Dis. 1985; 152:560-5
30. TAVECHIO, A. T.; GHILARDI, A. C. R.; PERESI, J. T. et al. *Salmonella* serotypes isolated from nonhuman sources in S Paulo, Brazil, from 1996 through 2000. J. Food protect., 65: 1041-1044, 2002.
31. THEOPHILO, G. N. D. & VIEIRA, R. H. S. F. Pesquisa de *Vibrio parahaemolyticus* em caranguejos crus e cozidos comercializados na Praia do Futuro (Fortaleza, C E). Bol. SBCTA, 28: 134-142, 1994.
32. VIEIRA, R. H. S. F. & IARIA, S. T.—*Vibrio parahaemolyticus* in lobster *Panulirus laevicauda* (Latreille). Rev. Microbiol. (S. Paulo), 24: 16-21, 1993.
33. Puglielli L, Cattrini C, Garces Resa J J, Velasques M, Leon Garcia L M Symptomless carriage of *Vibrio cholerae* in Peru. Lancet. 1992 Apr. 25; 339(8800):1056-7
34. Parkinson R, Rajic A, Jenson C. Investigation of an anthrax outbreak in Alberta in 1999 using a geographic information system. Agriculture and Agri-Food Canada, 600, 138-4th Avenue Southeast, Calgary, Alberta T2G 4Z6.
35. Watson J, Koya V, Leppla S H, Daniell H Expression of *Bacillus anthracis* protective antigen in transgenic chloroplasts of tobacco, a non-food/feed crop. Vaccine. 2004 Oct. 22; 22(31-32):4374-84 Department of Molecular Biology and Microbiology, University of Central Florida, Biomolecular Science Building #20, Room 336, Orlando, Fla. 32816-2364, USA.
36. Jarque I, Andreu R, Salayert M, Gomez D, Peman J, Gobernado M, Sanz M A.[Value of *Aspergillus galactomannan* antigen detection in the diagnosis and follow-up of invasive aspergillosis in hematological patients]
37. Jimenez-Gasco M M, Navas-Cortes J A, Jimenez-Diaz R M. The *Fusarium oxysporum* f. sp. *ciceris*/*Cicer arietinum* pathosystem: a case study of the evolution of plant-pathogenic fungi into races and pathotypes. Int Microbiol. 2004 June; 7(2):95-104
38. Lievens B, Brouwer M, Vanachter A C, Cammue B P, Thomma B P Rapid detection and identification of tomato vascular wilt pathogens using a DNA array. Commun Agric Appl Biol Sci. 2003; 68(4 Pt B):569-81
39. Okhovvat S M, Zakeri Z Identification of fungal diseases associated with imported wheat in Iranian silos. Commun Agric Appl Biol Sci. 2003; 68(4 Pt B):533-5
40. Lievens B, Brouwer M, Vanachter A C, Levesque C A, Cammue B P, Thomma B P Design and development of a DNA array for rapid detection and identification of multiple tomato vascular wilt pathogens. FEMS Microbiol Lett. 2003 Jun. 6; 223(1):113-22

What is claimed is:

1. A process of increasing an antimicrobial activity of an antimicrobial plant extraction liquid, comprising a step of ionizing silver in the plant extraction liquid used as an electrolyte by means of electrolysis, wherein the plant extraction liquid is a plant extraction liquid selected from the group consisting of an oak tree extraction liquid, a pine tree extraction liquid, a thuja extraction liquid and a marine algae extraction liquid.

2. The process of claim 1, wherein the antimicrobial activity is effective against a microbe selected from the group consisting of *Escherichia* sp., *Salmonella* sp., *Bacillus* sp. *Staphylococcus* sp., *Vibrio* sp., *Aeromonos* sp., *Chromobacteria* sp., *Streptococcus* sp., *Lactobacillus* sp. *Aspergillus* sp., *Fusarium* sp., *Trichoderma* sp., *Trichophyton* sp., *Microsporum* sp. and *Candida* sp.

* * * * *